United States Patent [19]
Benjamin et al.

[11] 4,149,551
[45] Apr. 17, 1979

[54] METHOD OF CONDITIONING HAIR USING A FLEXIBLE SUBSTRATE

[75] Inventors: Lawrence Benjamin; Craig R. Carson, both of Cincinnati, Ohio

[73] Assignee: The Procter & Gamble Company, Cincinnati, Ohio

[21] Appl. No.: 781,822

[22] Filed: Mar. 28, 1977

[51] Int. Cl.² ............................................. A45D 7/00
[52] U.S. Cl. ........................................... 132/7; 424/70
[58] Field of Search ............... 132/7, 88.7; 424/70; 427/240, 248

[56] References Cited

U.S. PATENT DOCUMENTS

| | | | |
|---|---|---|---|
| 3,056,154 | 10/1962 | Neal | 15/104 |
| 3,206,362 | 9/1965 | Hollub | 132/7 |
| 3,395,041 | 7/1968 | Hsiung | 132/7 |
| 3,442,692 | 5/1969 | Gaiser | 427/240 |
| 3,678,157 | 7/1972 | Kalopissis | 132/7 |
| 3,679,102 | 7/1972 | Charle | 132/88.7 |
| 3,728,447 | 4/1973 | Osipow | 132/7 |
| 3,790,664 | 2/1974 | Krochock | 132/7 |
| 3,822,312 | 7/1974 | Sato | 424/7 |
| 3,954,113 | 5/1976 | Bohrer | 132/7 |

Primary Examiner—G. E. McNeill
Attorney, Agent, or Firm—Douglas C. Mohl; Richard C. Witte

[57] ABSTRACT

A method of conditioning hair comprises rubbing the hair with an article comprised of a flexible substrate having releasably associated therewith a normally solid substantially water-insoluble hair conditioning agent. The article provides combing, detangling, static flyaway, softness, luster, and manageability benefits.

20 Claims, No Drawings

METHOD OF CONDITIONING HAIR USING A FLEXIBLE SUBSTRATE

BACKGROUND OF THE INVENTION

The subject invention relates to a method of conditioning hair. More particularly, hair is conditioned by use of a flexible substrate having a hair conditioning agent releasably affixed thereto. Preferably, the article is used after shampooing and prior to drying.

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. A variety of approaches have been developed to alleviate the after-shampoo problems. These range from the inclusion of hair conditioning aids in shampoos to post-shampoo application of hair conditioners, i.e. hair rinses. Difficulties associated with the use of conditioning aids in shampoos have been compatibility problems and a greasy feel on the just-washed hair. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient. The results obtained in this manner also have not been fully satisfactory due to the difficulties associated with the deposition and retention on the hair of the hair conditioning aid.

It is an object of this invention to provide a method of conditioning hair so as to impart thereto combing, detangling, static fly-away, softness, luster, and manageability benefits.

It is another object of this invention to provide a method of conditioning hair using an article comprising a flexible substrate and a hair conditioning agent.

A still further object of this invention is to provide a method for conditioning hair after a shampoo with a flexible article having releasably associated therewith a normally solid substantially water-insoluble hair conditioning agent.

These and other objects of the invention will become apparent from the description to follow.

As used herein, all percents and ratios are by weight unless otherwise indicated.

SUMMARY OF THE INVENTION

A method of conditioning hair to provide combing, detangling, static fly-away, softness, luster, and manageability benefits comprising rubbing the hair with an article comprised of a flexible substrate having releasably associated therewith from 0.2 gram to 15 grams per square meter of substrate of a normally solid substantially water-insoluble hair conditioning agent, said agent selected from the group consisting of a quaternary ammonium salt, quaternary imidazolinium salt, fatty alcohol, sorbitan ester, polyhydric alcohol ester, fatty acid salt, aliphatic ether, and mixtures thereof, said rubbing causing the transfer of an effective amount of hair conditioning agent to the hair.

DETAILED DESCRIPTION OF THE INVENTION

The method of this invention comprises rubbing the hair with a flexible substrate. The flexible substrate has a normallly solid substantially water-insoluble hair conditioning agent associated with it. Rubbing of the hair transfers the hair conditioning agent from the flexible substrate to the hair. The article herein provides convenience as well as performance benefits, i.e. combing, detangling, static fly-away, softness, luster, and manageability benefits. "Manageability" is used in the sense the hair is given a pleasing appearance due to the body and control imparted to the hair by the hair conditioning agent. Drying benefits are also achieved when the article is used on wet hair. The manner of use of the article is described in greater detail hereinafter.

The article used herein comprises a flexible substrate together with a hair conditioning agent. The flexible substrate comprises from 0.2 gram to 15 grams, preferably 1 gram to 7 grams, most preferably 1.5 grams to 4.5 grams conditioning agent per square meter of substrate. A level of conditioning agent below 0.2 gram is avoided because of a lack of noticeable benefits while a level above 15 grams is avoided because of excessive conditioning agent transfer to the hair, a noticeable build-up of conditioning agent on the comb, and an unpleasant feeling on the hands of the user. The article described in detail in the succeeding paragraphs.

FLEXIBLE SUBSTRATE

Suitable substrates include flexible paper, woven cloth and non-woven cloth. The substrate can have a dense structure, e.g. a one-ply or ordinary kraft paper, or more preferably, an open or porous structure.

Open or porous substrates of a paper, woven cloth or non-woven cloth nature useful herein are fully disclosed in U.S. Pat. No. 3,686,025, Morton, TEXTILE SOFTENING AGENTS IMPREGNATED INTO ABSORBENT MATERIALS, issued Aug. 22, 1972, incorporated herein by reference. These substrates are considered to be absorbent; the term "absorbent", as used herein, is intended to mean a substance with an absorbent capacity (i.e., a parameter representing a substrate's ability to take up and retain a liquid) from 5.5 to 12, preferably 7 to 10, times its weight of water.

The preferred substrates used in this invention can also be defined in terms of "free space". Free space, also called "void volume", as used herein is intended to mean that space within a structure that is unoccupied. For example, certain multi-ply paper structures comprise plies embossed with protuberances, the ends of which are mated and joined; this paper structure has a void volume or free space between the fibers of the paper sheet itself. A non-woven cloth also has free space between each of its fibers. The free space of non-woven cloth or paper, having designated physical dimensions, can be varied by modifying the density of the paper or non-woven cloth. Substrates with a high amount of free space generally have low fiber density; high density substrates generally have a low amount of free space.

A suitable paper substrate comprises a compressible, laminated, calendered, multi-ply, absorbent paper structure. Preferably, the paper structure has 2 or 3 plies and a total basis weight of from 20 to 140 grams per square meter and absorbent capacity values within the range of 7 to 10. Each ply of the preferred paper structure has a basis weight of about 3 to 13 kilograms per 280 square meters, and the paper structure can consist of plies having the same or different basis weights. Each ply is preferably made from a creped, or otherwise extensible, paper with a creped percentage of about 15% to 40% and a machine direction (MD) tensile and cross-machine (CD) tensile of from about 15 to 230 grams per square cm of paper width. The two outer plies of a 3-ply paper structure or each ply of a 2-ply paper structure are embossed with identical repeating patterns consisting of about 2.5 to 30 discrete protuberances per square cm, raised to a height of from about 0.25 cm to 1 cm above the surface of the unembossed paper sheet. From about 10% to 60% of the paper sheet surface is raised. The distal ends (i.e. the ends away from the unembossed paper sheet surface) of the protuberances on each ply are mated and adhesively joined together, thereby providing a preferred paper structure exhibiting a compressive modulus of from about 31 to 120 cm-grams per cubic cm and Handle-O-Meter (HOM) MD and CD values of from about 10 to 130.

Suitable adhesives for multi-ply paper are known in the art and include water, starches, wet-strength resins, and polyvinyl acetates. A particularly suitable adhesive is prepared by heating from about 2 to about 4 parts by weight of substantially completely hydrolyzed polyvinyl alcohol resin in from about 96 to about 98 parts by weight of water. Preferably, about 0.04 grams of adhesive solids are used to join a square meter of the embossed plies, with the adhesive being applied to the distal surfaces of the protuberances of one or all plies.

The compressive modulus values which define the compressive deformation characteristics of a paper structure compressively loaded on its opposing surfaces, the HOM values which refer to the stiffness or handle of a paper structure, the MD and CD HOM values which refer to HOM values obtained from paper structure samples tested in a machine and cross-machine direction, the methods of determining these values, the equipment used, and a more detailed disclosure of the paper structure preferred herein, as well as methods of its preparation, can be found in U.S. Pat. No. 3,414,459, Wells, COMPRESSIBLE LAMINATED PAPER STRUCTURE, issued Dec. 3, 1968, the disclosures of which are incorporated herein by reference.

The preferred non-woven cloth substrates used in the invention herein are generally defined as adhesively bonded fibrous or filamentous products having a web or carded fiber structure (where the fiber strength is suitable to allow carding), or comprising fibrous mats in which the fibers or filaments are distributed haphazardly or in random array (i.e., an array of fibers in a carded web wherein partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, poly-olefins, polyamides, or polyesters).

Methods of making non-woven cloths are not a part of this invention and, being well known in the art, are not described in detail herein. Generally, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, dried, cured, and otherwise treated as desired to form the non-woven cloth. Non-woven cloths made of polyesters, polyamides, vinyl resins, and other thermoplastic fibers can be spun-bonded, i.e., the fibers are spun out onto a flat surface and bonded (melted) together by heat or by chemical reactions.

The absorbent properties required with non-woven clothes are provided merely by building up the thickness of the cloth, i.e. by superimposing a plurality of carded webs or mats to a thickness adequate to obtain the necessary absorbent properties, or by allowing a sufficient thickness of the fibers to deposit on the screen. Any diameter or denier of the fiber (generally up to about 10 denier) can be used, inasmuch as it is the free space between each fiber that makes the thickness of the cloth directly related to the absorbent capacity of the cloth, and which, further, makes the non-woven cloth especially suitable for impregnation with a hair conditioning agent by means of intersectional or capillary action. Thus, any thickness necessary to obtain the required absorbent capacity can be used.

The choice of binder-resins used in the manufacture of non-woven cloths provides substrates possessing a variety of desirable traits. For example, the absorbent capacity of the cloth is increased, decreased, or regulated by respectively using a hydrophilic binder-resin, a hydrophobic binder-resin, or a mixture thereof, in the fiber bonding step.

When the substrate for the articles herein is a non-woven cloth made from fibers deposited haphazardly or in random array on the screen, the articles exhibit excellent strength in all directions and are not prone to tear or separate when used in the hair conditioning method.

The preferred non-woven cloth is water-laid or air-laid and is made from cellulosic fibers, particularly from regenerated cellulose, polyester or polyolefin, which are lubricated with any standard textile lubricant. Preferably, the fibers are from 0.45 cm to 5 cm in length and are from 1.5 to 5 denier. Preferably, the fibers are at least partially oriented haphazardly, particularly substantially haphazardly, and are adhesively bonded together with a hydrophobic or substantially hydrophobic binder-resin, particularly with a nonionic self-cross-linking acrylic polymer or polymers. Preferably, the cloth comprises about 70% fiber and 30% binder-resin polymer by weight and has a basis weight of from 20 to 80 grams per square meter.

Woven cloths are the single or double knit cloths made from natural fibers, (e.g. cotton or wool) synthetic fibers (e.g. rayon, polypropylene or polyester) or fiber blends (e.g. a cotton/polyester blend). Such cloths have a basis weight of from 20 to 140 grams per square meter.

It will be recognized certain of the above substrates are absorbent and are capable of providing some drying when used on wetted hair. The drying provided by these substrates represents a benefit in addition to those previously discussed benefits achieved through the transfer of the hair conditioning agent to the hair.

HAIR CONDITIONING AGENT

The hair conditioning agent releasably associated with the above described flexible substrate is a normally solid, i.e. solid at temperatures below 30° C., substantially water-insoluble, i.e. having a water-solubility of less than 1% at 30° C., compound. It is selected from the group consisting of quaternary ammonium salts, quaternary imidazolinium salts, sorbitan esters, fatty alcohols, polyhydric alcohol esters, fatty acid salts, aliphatic ethers, and mixtures thereof. The quaternary ammonium salts are preferred. In addition to their combing, detangling, softness, luster and manageability benefits, they provide excellent static fly-away benefits. The individual classes of hair conditioning agents are discussed in the following paragraphs.

Quaternary ammonium salts have the formula:

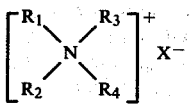

wherein $R_1$ is hydrogen, an aliphatic group of from 1 to 22 carbon atoms, or aromatic, aryl or alkaryl groups having 6 to 20 carbon atoms; $R_2$ is an aliphatic group having from 12 to 22 carbon atoms; $R_3$ and $R_4$ are each alkyl groups of from 1 to 3 carbon atoms; and X is an anion selected from halogen, acetate, phosphate, nitrate and methyl sulfate radicals.

Preferably quaternary ammonium salts are the dialkyl dimethyl ammonium chlorides, wherein the alkyl groups have from 12 to 22 carbon atoms and are derived from long-chain fatty acids, such as hydrogenated tallow. The term "tallow" refers to fatty alkyl groups derived from tallow fatty acids. Such fatty acids give rise to quaternary compounds wherein $R_1$ and $R_2$ have predominantly from 16 to 18 carbon atoms. The term "coconut" refers to fatty acid groups from coconut oil fatty acids. The coconut-alkyl $R_1$ and $R_2$ groups have from 8 to about 18 carbon atoms and predominate in $C_{12}$ to $C_{14}$ alkyl groups.

Representative examples of quaternary ammonium salts of the invention include ditallow dimethyl ammonium chloride; ditallow dimethyl ammonium methyl sulfate; dihexadecyl dimethyl ammonium chloride; di(-hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium acetate; dihexadecyl diethyl ammonium chloride; dihexadecyl dimethyl ammonium acetate; ditallow dipropyl ammonium phosphate; ditallow dimethyl ammonium nitrate; di(coconut-alkyl) dimethyl ammonium chloride; and stearyl dimethyl benzyl ammonium chloride.

Other quaternary ammonium salts useful herein are the compounds of the formula

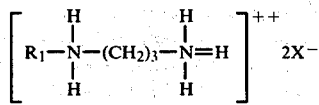

wherein $R_1$ is an aliphatic group having 16 to 22 carbon atoms and X is an anion as above defined. Tallow propanediamine hydrochloride is an example of this quaternary ammonium salt.

Quaternary imidazolinium salts have the formula

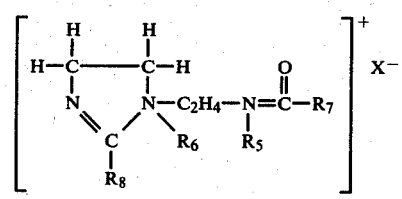

wherein $R_6$ is an alkyl group containing from 1 to 4, preferably from 1 to 2 carbon atoms, $R_5$ is an alkyl group containing from 1 to 4 carbon atoms or a hydrogen radical, $R_8$ is an alkyl group containing from 1 to 22, preferably at least 15 carbon atoms or a hydrogen radical, $R_7$ is an alkyl group containing from 8 to 22, preferably at least 15 carbon atoms, and X is an anion, preferably chloride. Other suitable anions include those disclosed with reference to the quaternary ammonium salts described hereinbefore.

Particularly preferred are those imidazolinium salts in which both $R_7$ and $R_8$ are alkyl of from 12 to 22 carbon atoms, e.g., 1-methyl-1-[(stearoylamide)ethyl]-2-heptadecyl-4,5-dihydroimidazolinium chloride; 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate.

The sorbitan esters are the esterified cyclic dehydration products of sorbitol, i.e., sorbitan ester. Sorbitol, itself prepared by catalytic hydrogenation of glucose, is dehydrated in well known fashion to form mixtures of cyclic 1,4- and 3,5-sorbitol anhydrides and small amounts of isosorbides. (See Brown; U.S. Pat. No. 2,322,821; issued June 29, 1943.) The resulting complex mixtures of cyclic anhydrides of sorbitol are collectively referred to herein as "sorbitan". It will be recognized that this "sorbitan" mixture will also contain some free uncyclized sorbitol.

Sorbitan esters useful herein are prepared by esterifying the "sorbitan" mixture with a fatty acyl group in standard fashion, e.g., by reaction with a fatty ($C_{10}$–$C_{24}$) acid or fatty acid halide. The esterification reaction can occur at any of the available hydroxyl groups, and various mono-, di-, etc., esters can be prepared. In fact, complex mixtures of mono-, di-, tri-, and tetra-esters almost always result from such reactions, and the stoichiometric ratios of the reactants can simply be adjusted to favor the desired reaction product.

The foregoing complex mixtures of esterified cyclic dehydration products of sorbitol (and small amounts of esterified sorbitol) are collectively referred to herein as "sorbitan esters". Sorbitan mono- and di-esters of lauric, myristic, palmitic, stearic and behenic acids are particularly useful herein. Mixed sorbitan esters, e.g. mixtures of the foregoing esters, and mixtures prepared by esterifying sorbitan with fatty acid mixtures such as the mixed tallow and hydrogenated palm oil fatty acids, are useful herein and are economically attractive. Unsaturated $C_{10}$–$C_{18}$ sorbitan esters, e.g., sorbitan monooleate, usually are present in such mixtures. It is to be recognized that all sorbitan esters, and mixtures thereof, which are essentially water-insoluble and which have fatty hydrocarbyl "tails", are materials in the context of the present invention.

The preferred alkyl sorbitan ester materials herein comprise sorbitan monomyristate, sorbitan monopalmitate, sorbitan monostearate, sorbitan monobehenate, sorbitan dilaurate, sorbitan dimyristate, sorbitan dipalmitate, sorbitan distearate, sorbitan dibehenate, and mixtures thereof, the mixed coconutalkyl sorbitan mono- and di-esters and the mixed tallowalkyl sorbitan mono- and di-esters. The tri- and tetra-esters of sorbitan with lauric, myristic, palmitic, stearic and behenic acids, and mixtures thereof, are also useful herein.

Another useful type of hair conditioning agent is the substantially water-insoluble compounds chemically classified as fatty alcohols. Mono-ols, di-ols, and poly-ols having the requisite melting points and water-insolubility properties set forth above are useful herein.

A preferred type of alcohol useful herein includes the higher melting members of the so-called fatty alcohol class. Although once limited to alcohols obtained from natural fats and oils, the term "fatty alcohols" has come to mean those alcohols which correspond to the alcohols obtainable from fats and oils, and all such alcohols can be made by synthetic processes. Fatty alcohols prepared by the mild oxidation of petroleum products are useful herein. Preferred fatty alcohols are saturated and have from 14 to 18 carbon atoms.

Examples of satisfactory alcohols are 1-tricosanol, 1-tetradecanol, 1-hexadecanol, 1-heptadecanol, 1-octadecanol, 1-eicosanol, 15-methyl hexadecanol, 1-heneicosanol, 2-octadecanol, 2-eicosanol, 1,1-diphenyl hexadecanol, 4-methylbenzyl alcohol, 1,12-octadecanediol, and 1,10-decanediol.

Another type of hair conditioning agent useful in the instant invention encompasses various esters of polyhydric alcohols. Polyhydric alcohols (e.g. glycerol, pentaerythritol and ethylene glycol) are reacted with a fatty acid containing 8 to 20 carbon atoms in well-known fashion to produce the polyhydric alcohol esters. Such compounds can be fully esterified or can have one or more free hydroxyl groups provided they have a melting point within the range recited herein and are substantially water-insoluble.

Esters of glycerol useful herein include the mono-, di- and tri-glycerides. The fatty acid groups on the glycerides contain from 8 to 20 carbon atoms. In particular, di-glycerides containing two $C_8$–$C_{20}$, preferably $C_{10}$–$C_{18}$, alkyl groups in the molecule are useful hair conditioning agents.

Non-limiting examples of polyhydric alcohol esters useful herein include: glycerol-1,2-dilaurate; glycerol-1,3-dilaurate; glycerol-1,2-dimyristate; glycerol-1,3-dimyristate; glycerol-1,2-dipalmitate; glycerol-1,3-dipalmitate; glycerol-1,2-distearate; glycerol-1,3-distearate; glycerol-1,2,3-trimyristate; butane tetra-ol-1,2,3-tristearate; ethylene glycol monostearate; and ethylene glycol distearate. Mixed glycerides available from mixed tallowalkyl fatty acids, i.e., 1,2-ditallowalkyl glycerol, 1,3-ditallowalkyl glycerol, and 1,2,3-tritallowalkyl glycerol are economically attractive for use herein. The foregoing esters are preferred for use herein due to their ready availability from natural fats and oils.

Fatty acid salts, especially the salts of the fatty acids having from 8 to 20 carbon atoms are used herein. Such salts are prepared by neutralizing the free fatty acids with a metallo base, e.g. $Mg(OH)_2$ or $Ca(OH)_2$ in well known fashion.

Examples of suitable fatty acid salts include calcium dodecanate, calcium tetradecanate, aluminum hexadecanate, magnesium hexadecanate, calcium eicosate, calcium 5-methyloctadecanate, magnesium 6-methyloctadecanate and calcium 2-hexadecanate.

Long chain aliphatic ethers with at least one hydrocarbon moiety containing 10 to 22 carbon atoms, including mono- and poly-ether alcohols having at least one free —OH group, also are useful hair conditioning agents. The ether-alcohols are prepared by the classic Williamson ether synthesis. Ethers useful herein include glycerol-1,2-dilauryl ether; glycerol-1,3-distearyl ether; butane tetra-ol-1,2,3-trioctanyl ether; ethylene glycol monolauryl ether; and propylene glycol monolauryl ether.

An optional component of the hair conditioning article are substantially water-insoluble particulate materials having a particle diameter ranging from 1 micron to 100 microns, preferably 10 microns to 30 microns. The particulate material provides additional combing and drying benefits to the article. When the hair is rubbed with the hair conditioning article, the particulate material is transferred to the hair and becomes enmeshed in the hair strands. It is believed the particulate material prevents the individual hair strands from becoming tangled; the resultant strands are easier to dry because of better drying-air contact with the unmatted hair. A particle diameter of less than 1 micron is avoided due to a noticeable lack of benefits as above described while a particle diameter above 100 microns is avoided because of the unsightly nature of such particles in the hair.

The water-insoluble particulate material is selected from the group consisting of starch, synthetic polymeric beads, glass beads, ceramic beads and mixtures thereof. D.O.S. 2,546,505 (published Apr. 29, 1976) gives a listing of such water-insoluble particulate materials and is herein incorporated by reference.

A level of from 0.1 gram to 10 grams, preferably 1 gram to 5 grams water-insoluble particulate material per square meter substrate is used to provide the additional combing and drying benefits.

METHOD-OF-MANUFACTURE

Impregnation or coating the substrate with the hair conditioning agent is done in any convenient manner, many methods being known in the art. For example, the hair conditioning agent in liquid form can be sprayed onto the substrate or can be added to a wood-pulp slurry from which the substrate is manufactured.

In one method of making the articles the hair conditioning agent is applied to the substrate by a method generally known as padding. The agent is applied in liquid (melted) form to the substrate from a pan or trough. A roll of substrate is set up on an apparatus so it can unroll freely. As it unrolls, it travels downwardly and submersed, passes through the pan or trough containing the liquified agent at a speed slow enough to allow sufficient impregnation. The substrate then travels upwardly and through a pair of rollers which removes excess liquid. The impregnated substrate is then cooled to room temperature after which it can be folded, cut or perforated at uniform lengths and subsequently packaged and/or used.

In another method the hair conditioning agent, in either a molten form or solution form, is sprayed onto the substrate as it unrolls and any excess agent is then squeezed off by the use of squeeze rollers or by a doctor-knife. This variation allows the substrate to be treated usually on one side only. Articles having the hair conditioning agent only on one side are preferred due to their better hand feel during use. This variation can optionally involve the use of metal rollers which are heated to maintain the agent in the liquid form.

Another method of manufacture involves the printing of molten or a solution-form of hair conditioning agent onto the substrate. The level of agent applied is controlled by the proper selection of gravure printing roll. The freshly applied hair conditioning agent is solidified either by a cooling step or a solvent evaporation step.

The resultant treated substrate is flexible. Sheet articles are manufactured from the treated substrate. The treated substrate is optionally slitted at any convenient time during the manufacturing process and packaged as sheets or in rolls. Such articles are of any shape or size, but preferably are rectangular or square in shape and range in size from 7 cm×10 cm to 50 cm×80 cm. It should be understood other shapes are intended to be covered and depend only upon the preferences of the consumer. For example, oval shaped articles as well as articles fabricated to fit over the hand for easier application are feasible.

USAGE

The hair conditioning article above described provides its benefits when rubbed against the hair of the user. The rubbing transfers the normally solid substantially water-insoluble conditioning agent from the substrate to the hair. The amount and point of placement of the agent on the hair is controlled by the user. Thus, the ends of the hair can be treated with a greater amount of conditioning agent than is applied to the roots of the hair. This allows for better hair conditioning and ease-of-combing benefits.

The article can be used in conjunction with the treatment of dry hair. Preferably, however, the article is used on hair which has just been shampooed and partially dried. The delivery of benefits above described is more easily accomplished when the hair is wet. After conditioning the hair in the above manner, the hair is dried in the normal fashion. It has been found less drying time is needed because of the fact that the hair is less tangled, i.e. individual hair strands are not matted together and thus can more easily be dried.

It will be recognized the method of conditioning hair above described, offers substantial benefits over the more conventional use of liquid hair rinses. Convenience benefits alone are substantial; no additional rinse applications (which can be messy) and fresh water rinse-aways are needed. Performance benefits are also substantial. The proper amount of conditioning agent is better controlled by using the method of this invention as well as its area of placement on the hair. Thus, the consumer can apply a level of conditioning agent by feel and appearance to portions of the hair needing it, i.e. usually near the ends of the hair when tangling problems and lack of desirable levels of sebum occur.

The following examples are illustrative of the invention hereindescribed.

EXAMPLE I

An article used in the method of this invention is manufactured as follows. A 4% solution of ditallow dimethyl ammonium chloride (DTDMAC) in isopropyl alcohol is made. A 25 cm wide roll of non-woven rayon/polypropylene (80/20, basis weight=60 grams/m$^2$) is positioned so as to easily unroll. As the roll of substrate is unwound and led through a spray booth, 6-7 ml of the solution per 580 square cm substrate is sprayed evenly on one side of the substrate. The sprayed portion of the substrate passes through a drying zone where the isopropyl alcohol evaporates. The treated substrate is cut every 23 cm and packaged. The resultant sheets contain the DTDMAC evenly distributed on one side at a level of 3.1 grams/m$^2$.

EXAMPLE II

Another manner of manufacturing the articles described herein utilizes a gravure printing cylinder. A 40% solution of ditallow dimethyl ammonium chloride (DTDMAC) in isopropyl alcohol is made. A rayon/polypropylene substrate, as used in Example I, is led from a 23 cm roll into the nip formed by a gravure printing cylinder and a back-up roll. The printing cylinder, rotating in a trough containing the DTDMAC solution, prints 0.5 grams solution onto one side of the substrate every 25 cm in a uniform pattern. The printed substrate is fed into a drying zone where the isopropyl alcohol evaporates, leaving a substrate having 3.1 grams DTDMAC/m$^2$ substrate. The substrate is cut into lengths 25 cm long and packaged.

EXAMPLE III

The following articles are manufactured:

| Substrate | Hair Conditioning Agent | Substrate Size (cm × cm) | Level of Hair Condition Agent (grams/square meter) |
| --- | --- | --- | --- |
| Paper* | Ditallow dimethyl ammonium chloride | 56 × 92 | 4.5 |
| Paper* | Stearyl dimethyl benzyl ammonium chloride | 56 × 92 | 4.5 |
| Non-woven polyester (basis wt. = 36 grams/m$^2$) | Ditallow dimethyl ammonium chloride | 23 × 25 | 3.0 |
| Non-woven rayon/polypropylene (80/20, basis wt. = 60 grams/m$^2$) | Ditallow dimethyl ammonium chloride | 23 × 25 | 1.5 |
| Non-woven rayon/polypropylene (80/20, basis wt. = 60 grams/m$^2$) | Ditallow dimethyl ammonium chloride/cetyl alcohol (2:1) | 7 × 10 | 3.1 |
| Non-woven wood pulp/polyester | Ditallow dimethyl ammonium chloride | 23 × 25 | 2.7 |
| Non-woven rayon | Ditallow dimethyl ammonium chloride | 23 × 25 | 3.0 |
| Cotton terry cloth | Stearyl dimethyl benzyl ammonium chloride | 32 × 32 | 12.7 |
| Non-woven rayon/polypropylene (80/20, basis wt. = 60 grams/m$^2$) | Cetyl alcohol | 23 × 25 | 3.1 |
| Non-woven rayon/polypropylene (80/20, basis wt. = 60 grams/m$^2$) | Sorbitan monostearate | 20 × 25 | 10.0 |
| Non-woven rayon/polypropylene (80/20, basis wt. = 60 grams/m$^2$) | Ethylene glycol monostearate | 15 × 30 | 2.0 |
| Non-woven rayon/polypropylene (80/20, basis wt. = 60 grams/m$^2$) | Calcium oleate | 30 × 30 | 8.1 |

*The paper substrate is a non-woven nylon reinforced paper sold under the brand name Kaycel and is available from Kimberly Clark Corp. It has a basis wt. of about 100 grams/m$^2$.

The above articles are individually evaluated by a group of panelists. Each panelist's hair is shampooed by a trained operator and is then rinsed. The articles are rubbed on the hair, the exact placement and degree of rubbing being determined by the preferences of the panelists. Comments from the panelists indicate the articles provide better comb-out, less tangling, static-fly-away control as well as imparting a more pleasing appearance to the hair as evidenced by good luster, softness, and manageability when compared to simply shampooing and rinsing the hair.

The same panelists indicated the aforedescribed benefits derived from the articles of the invention are at least comparable in all respects to the benefits obtained when the hair is shampooed, rinsed, treated with a commercially available hair rinse, and rinsed again. (The hair rinse contains stearly dimethyl benzyl ammonium chloride, cetyl alcohol, water and perfume.) The use of the article is more convenient and less messy to use.

EXAMPLE IV

Articles made of a non-woven rayon/polypropylene substrate (80/20, basis weight=60 grams/m$^2$) having varying levels of a ditallow dimethyl ammonium chloride hair conditioning agent as indicated below are compared. The articles have a rectangular shape of 23 cm×25 cm and are coated on one side of the substrate.

| Article | Hair Conditioning Agent Level |
| --- | --- |
| A | 0.1 grams/m$^2$ |
| B | 3.0 grams/m$^2$ |
| C | 40.0 grams/m$^2$ |

Article B is illustrative of the article used in the method of this invention.

Over-the-shoulder length hair is shampooed, rinsed and treated individually with Articles A, B, and C. Article A provides an unsatisfactory level of benefits due to its low hair conditioning agent level.

Article B provides combing, detangling, static-fly-away, luster, softness and manageability benefits, the degree of which is controlled by the individual in rubbing the hair with the article.

Article C gives a greasy feel on the hand of the user as well as transfers an excessive level of hair conditioning agent to the hair of the user. The excessive level of agent gives a greasy feel and appearance to the hair. A noticeable build-up of the agent on the comb of the user is also objectionable. An objectionable resoiling problem and perceived need for another shampoo is noted.

What is claimed is:

1. A method of conditioning hair to provide combing, detangling, static fly-away, softness, luster, and manageability benefits comprising rubbing the hair with an article comprised of a flexible substrate having reasonably associated therewith from 0.2 gram to 15 grams per square meter of substrate of a normally solid substantially water-insoluble hair conditioning agent, said agent selected from the group consisting of a quaternary ammonium salt, quaternary imidazolinium salt, fatty alcohol, sorbitan ester, polyhydric alcohol ester, fatty acid salt, aliphatic ether, and mixtures thereof, said rubbing causing the transfer of an effective amount of hair conditioning agent to the hair.

2. The method of claim 1 wherein the flexible substrate is selected from the group consisting of paper, woven cloth and non-woven cloth.

3. The method of claim 2 wherein from 1 gram to 7 grams of the conditioning agent per square meter of flexible substrate is present on the article.

4. The method of claim 3 wherein from 1.5 grams to 4.5 grams of the conditioning agent per square meter of flexible substrate is present on the article.

5. The method of claim 3 wherein the flexible substrate is a non-woven cloth.

6. The method of claim 5 wherein the flexible substrate ranges in size from 7'10 centimeters to 50×80 centimeters.

7. The method of claim 2 wherein the hair is wetted prior to rubbing with the article.

8. The method of claim 7 wherein the hair conditioning agent is a quaternary ammonium salt.

9. The method of claim 3 additionally having releasably associated with the flexible substrate from 0.1 gram to 10 grams per square meter of substrate of a water-insoluble particulate material having a diameter of from 1 micron to 100 microns.

10. The method of claim 9 wherein the particulate material is selected from the group consisting of water-insoluble starch particles, synthetic polymeric beads, glass beads, ceramic beads, and mixtures thereof.

11. The method of claim 10 wherein the article has from 1 gram to 5 grams per square meter substrate of the water-insoluble particulate material, said material having a particle diameter of from 10 microns to 30 microns.

12. The method of claim 11 wherein the hair conditioning agent is a quaternary ammonium salt.

13. The method of claim 12 wherein the quaternary ammonium salt is ditallow dimethyl ammonium chloride.

14. A method of conditioning hair to provide combing, detangling, static fly-away, softness, luster, and manageability benefits comprising:
    (a) wetting the hair; and
    (b) rubbing the hair with an article comprised of a flexible non-woven cloth substrate having releasably associated therewith from 0.2 gram to 15 grams per square meter of substrate of a normally solid substantially water-insoluble quaternary ammonium salt, said rubbing causing the transfer of an effective amount of the quaternary ammonium salt to the hair.

15. The method of claim 14 wherein the article comprises from 1 gram to 7 grams of the quaternary ammonium salt.

16. The method of claim 15 wherein the article comprises from 1.5 grams to 4.5 grams of the quaternary ammonium salt.

17. The method of claim 15 wherein the flexible substrate ranges in size from 7×10 centimeters to 50×80 centimeters.

18. The method of claim 15 wherein the article is fabricated to fit over a hand for ease of application.

19. The method of claim 17 wherein the quaternary ammonium salt is ditallow dimethyl ammonium chloride.

20. The method of claim 18 wherein the quaternary ammonium salt is ditallow dimethyl ammonium chloride.

* * * * *